United States Patent
Favre et al.

(10) Patent No.: US 8,529,923 B2
(45) Date of Patent: Sep. 10, 2013

(54) COSMETIC COMPOSITION BASED ON SUBSTANTIALLY HEMISPHERICAL PARTICLES

(75) Inventors: Sophie Favre, Paris (FR); Sarah Sebban, Saint Quen (FR)

(73) Assignee: Chanel Parfums Beaute, Neuilly sur Seine (FR)

( * ) Notice: Subject to any disclaimer, the term of this patent is extended or adjusted under 35 U.S.C. 154(b) by 0 days.

(21) Appl. No.: 13/389,078

(22) PCT Filed: Aug. 4, 2009

(86) PCT No.: PCT/IB2009/054054
§ 371 (c)(1),
(2), (4) Date: Feb. 6, 2012

(87) PCT Pub. No.: WO2011/015907
PCT Pub. Date: Feb. 10, 2011

(65) Prior Publication Data
US 2012/0148645 A1 Jun. 14, 2012

(51) Int. Cl.
A61K 8/02 (2006.01)
A61K 8/00 (2006.01)
A61K 8/18 (2006.01)
A61Q 17/04 (2006.01)
A61Q 5/08 (2006.01)
A61Q 19/02 (2006.01)

(52) U.S. Cl.
USPC ............................... 424/401; 424/59; 424/62

(58) Field of Classification Search
USPC ....................................................... 424/401
See application file for complete search history.

(56) References Cited

U.S. PATENT DOCUMENTS

| | | | |
|---|---|---|---|
| 3,439,088 A | 4/1969 | Walter | |
| 3,818,105 A | 6/1974 | Coopersmith et al. | |
| 7,531,184 B2 * | 5/2009 | Horino et al. | 424/401 |
| 8,147,853 B2 * | 4/2012 | Taylor et al. | 424/401 |
| 2005/0002890 A1 | 1/2005 | Gardel et al. | |
| 2005/0100568 A1 * | 5/2005 | De Mul et al. | 424/401 |
| 2005/0118218 A1 | 6/2005 | Cassin | |
| 2005/0163730 A1 | 7/2005 | Rosevear et al. | |
| 2009/0013481 A1 * | 1/2009 | Colaco et al. | 8/426 |
| 2010/0204037 A1 * | 8/2010 | Gensler et al. | 502/159 |
| 2011/0014138 A1 * | 1/2011 | Romaine | 424/59 |

FOREIGN PATENT DOCUMENTS

| | | |
|---|---|---|
| JP | 2004-027008 | 1/2004 |
| JP | 2005-194212 | 7/2005 |
| JP | 2006-348266 | 12/2006 |
| JP | 2008-031137 | 2/2008 |
| JP | 2008-031138 | 2/2008 |

OTHER PUBLICATIONS

Kim et al. (2002). "Titanium dioxide/poly(methyl methacrylate) composite microspheres prepared by in situ suspension polymerization and their ability to protect against UV rays". Colloid Polym Sci., 280: 584-588.*
Tajima et al. (2008). "Hemisperical polymer nano-particles of polyisoprene-poly(methyl methacrylate) blend with core-shell structure". Colloids and Surfaces A: Physicochem. Eng. Aspects, 313-314: 332-334.*
Becker et al. (2003). "A fatal paramethoxymethamphetamine intoxication". Legal Medicine, 5: S138-S141.*
Encyclopædia Britannica. "polymethyl methacrylate (PMMA)." Encyclopædia Britannica Online. Encyclopædia Britannica Inc., 2012. Web. Jul. 24, 2012. <http://www.britannica.com/EBchecked/topic/1551203/polymethyl-methacrylate>.*
Machine Translation of JP2008031138 (A).*
Environmental Working Group (EWG) [retrieved on Feb. 6, 2013]. Retrieved on from the internet: <URL: http://www.ewg.org/skindeep/ingredient/706643/TRIETHOXYCAPRYLYL-SILANE/>.*
International Search Report dated May 18, 2010, corresponding to PCT/IB2009/054054.

* cited by examiner

*Primary Examiner* — Robert T Crow
*Assistant Examiner* — Doan Phan
(74) *Attorney, Agent, or Firm* — Young & Thompson

(57) ABSTRACT

Disclosed is a cosmetic composition including, in a cosmetically acceptable medium, the combination of (a) a sufficient amount of uncoated substantially hemispherical PMMA particles and (b) a sufficient amount of substantially hemispherical PMMA particles coated with optionally treated metal oxide. It also relates to its uses in caring for or making up the skin.

15 Claims, No Drawings

COSMETIC COMPOSITION BASED ON SUBSTANTIALLY HEMISPHERICAL PARTICLES

BACKGROUND OF THE INVENTION

Field of the Invention

The present invention relates to a cosmetic composition comprising, in a cosmetically acceptable medium, the combination: (a) of uncoated substantially hemispherical PMMA particles; (b) of substantially metal oxide. It also relates to its uses in caring for or making up the skin.

Use is conventionally made, in cosmetic products, of powders of various shapes, in particular spherical, lamellar or potatoid, composed of organic and/or inorganic materials.

The main role of these powders is to increase the slip of the cosmetic composition over the skin or lips, to reduce the feeling of greasiness on the skin by absorption of oils or to contribute softness to the skin or lips. In addition, lamellar powders increase the specular reflection of light and thus the gloss of the lips, while spherical or potatoid powders have a greater tendency to scatter light and to thus render the skin more matt.

In addition, depending on the opaqueness, these powders allow the skin to a greater or lesser extent to appear. Thus, covering powders can be used to correct deficiencies in uniformity of colour but they confer, on the make-up, a rather unnatural mask effect. Among them, pigments in addition have the disadvantage of absorbing light and thus reducing the luminosity of the skin. In order to overcome this disadvantage, the suggestion has been made to use corrective pigments of interference type which are less covering and make possible more subtle correction of surface irregularities. In particular, interference pigments with pink or orange glints can give an impression of looking well and of radiance. However, these pigments generally have a lamellar structure, so that they provide the skin with a shiny effect incompatible with correcting failings in skin relief (pores, wrinkles and fine lines). Furthermore, a glossy make-up is generally not desired by the consumer of cosmetic products, who likens it to the undesirable effect produced by greasy skin.

In order to correct irregularities in skin relief, recourse has been had, in a variant, to transparent powders which, by scattering light, produce the effect known under the name of "soft focus", that is to say that they smooth out, by an optical effect, the imperfections of the face, such as pores and wrinkles and fine lines. These powders sometimes have a tendency to mattify the skin and thus to bring about a decline in its luminosity and thus in its radiance. Furthermore, their transparency does not make it possible to correct deficiencies in uniformity of colour.

Consequently, the need remains to provide a means which makes it possible, in a composition for caring for or making up the skin, to improve the correction in the colour and in skin relief while contributing radiance.

In point of fact, the Applicant Company has now discovered that it is possible to use, for this purpose, the combination of two powders with a specific shape and with a specific composition in a cosmetic composition.

SUMMARY OF THE INVENTION

A subject-matter of the present invention is thus a cosmetic composition comprising, in a cosmetically acceptable medium, the combination:

(a) of uncoated substantially hemispherical PMMA particles;
(b) of substantially hemispherical PMMA particles coated with optionally treated metal oxide.

"PMMA" is understood to mean, within the meaning of the present invention, a methyl methacrylate homopolymer.

In addition, "substantially hemispherical" is understood to mean that the particles can exhibit the shape of a half-sphere or more generally of a portion of a solid sphere having a diameter/height ratio of between 2/1.2 and 2/0.5, limits included. It is also understood that the surface, in transverse cross section, of these hemispheres may not be perfectly circular, provided that the ratio of their greatest dimension (regarded as the "diameter") to their smallest dimension remains between 1.2/1 and 1/1, limits included. More generally, with regard to the definition and method for preparation of the substantially hemispherical particles of this invention, one can refer to the disclosure of JP2004-027008 which is incorporated herein by reference.

The uncoated hemispherical PMMA particles (a) of use for the invention can, for example, be those sold by Daito Kasei under the name of 3D Tech Plain® or by Sekisui Plastics Co. under the trade name LMX®.

The hemispherical PMMA particles (b) are coated with at least one metal oxide. Examples of such metal oxides can be found in JP2006-348266, JP2008-031137 and JP2008-031138. A preferred metal oxide is titanium dioxide which may be in the rutile form and preferably has a primary particles size of from 10 to 50 nm, more preferably from 15 to 40 nm and, better, from 30 to 40 nm. Its specific surface area may range from 20 to 120 $m^2/g$, preferably from 30 to 50 $m^2/g$. An example of such titanium dioxide particles is the product marketed by PRESPERSE LLC under the trade name MT-500SA®.

The coated hemispherical PMMA particles (b) can be prepared by a mechanical mixing process known to a person skilled in the art, starting from:

uncoated hemispherical PMMA particles (a) described above; and
a metal oxide having a primary particle size of between 1 nm and 100 nm, limits included.

The metal oxide layer at least partially, and preferably completely, covering the PMMA particles may or may not be treated. According to a preferred embodiment of the invention, the metal oxide is treated in order to prevent phenomena of photocatalysis. The treatments which can be used are for example, based:

on silicone derivatives, such as dimethicone, sold in particular under the name SA® by Maprecos,
on triethoxycaprylylsilane, sold in particular under the reference OTS® by Daito or 11S2® by Kobo,
on titanates, obtained in particular using isopropyl titanium triisostearate, for example sold under reference I2® by Kobo and described in U.S. Pat. No. 4,877,604,
on esters, such as isostearyl sebacate, sold in particular under the reference HS® by Miyoshi,
on fluorinated compounds, such as a perfluoroalkylethyl phosphate, sold under reference PF® by Daito,
or on their mixtures.

Preferably, use is made of a metal oxide, and in particular of titanium dioxide, treated with triethoxycaprylylsilane and in particular with the OTS® treatment from Daito.

DETAILED DESCRIPTION OF THE INVENTION

The metal oxide coating the PMMA can represent from 10 to 40% by weight, with respect to the total weight of the PMMA/metal oxide composite. Preferably, the metal oxide represents from 25 to 35% by weight and more preferably approximately 30% by weight, with respect to the total weight of the PMMA/metal oxide composite.

As indicated above, the process for the preparation of the substantially hemispherical PMMA particles coated with metal oxide(s) is a process of mechanical mixing of the PMMA particles and of the metal oxide(s), so as to obtain a homogeneous deposition of the metal oxide over the PMMA particles. It can in particular be a process as described in the document JP2006-348266 of Daito Kasei, incorporated by way of reference. Mention may in particular be made of the process described in Example 5 of this document.

In the composition according to the invention, the particles of (a) and of (b) are combined, preferably in a ratio by weight of (a) to (b) of between 20/80 and 80/20, more preferably in a ratio by weight of (a) to (b) of between 25/75 and 75/25 and better still in a ratio by weight of (a) to (b) of approximately 50/50.

Furthermore, the combination of these substantially hemispherical particles (a) and (b) can represent from 1 to 60% by weight, preferably from 2 to 25% by weight and more preferably from 2 to 10% by weight, with respect to the total weight of the composition comprising them.

This composition additionally comprises, as described above, a cosmetically acceptable medium. "Cosmetically acceptable medium" is understood to mean a physiologically acceptable medium, that is to say a medium compatible with the skin and which does not produce feelings of discomfort (redness, tightness, tingling, and the like) after application to the skin which are unacceptable to the user.

The composition according to the invention can be provided in the form of an oil-in-water (O/W) emulsion, of a water-in-oil (W/O) emulsion, such as a water-in-silicone (W/Si) emulsion, or of a multiple emulsion (W/O/W, O/W/O, and the like). The composition according to the invention can also be anhydrous, that is to say that it does not comprise water or at the very most the water naturally included in the ingredients present therein, that is to say at most 3% by weight of water, indeed even at most 1% by weight of water, with respect to the weight of the composition.

This composition can in particular be provided in the form of a fluid product, in the form of a gel or in the form of a semisolid product, such as a cream. It can also be provided in the form of a solid product, such as a loose powder, a compact powder or a stick.

The composition according to the invention can additionally comprise various adjuvants, such as at least one compound chosen from volatile or nonvolatile oils; fatty-phase structuring or lipophilic gelling agents; aqueous-phase structuring or hydrophilic gelling agents; pasty compounds; film-forming polymers; pressure-sensitive adhesive (PSA) polymers; emulsifiers; fillers; compounds having an optical effect, including colouring materials, such as pigments, optionally of interference or goniochromatic type, water-soluble or fat-soluble dyes, lakes and pearlescent agents; tightening agents; active agents for caring for the skin, in particular moisturizing agents (such as polyols), antioxidants, depigmenting antiageing agents and/or slimming agents; UV screening agents; sequestering agents, such as EDTA salts; pH adjustors; preservatives; fragrances; and their mixtures, without this list being limiting.

The oils can be chosen from linear silicones, cyclic silicones, hydrocarbons, synthetic (poly)esters and (poly)ethers, branched and/or unsaturated fatty alcohols (such as octyldodecanol or hexyldecanol), branched and/or unsaturated fatty acids (such as linoleic acid and linolenic acid), fluorinated oils, vegetable oils and their mixtures.

Mention may in particular be made, among linear silicones, of volatile and nonvolatile polydimethyl-siloxanes and in particular those of formula:

in which n is an integer from 0 to 7 and preferably from 0 to 5.

Mention may in particular be made, among cyclic silicones, of those of formula:

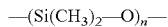

in which n is an integer from 3 to 6.

Linear and cyclic silicones are sold by numerous companies, such as, in particular, Dow Corning Corporation, Shin-Etsu, Siltech Corp. and Momentive Performance Materials (formerly GE Silicones). Mention may in particular be made of the silicones with the trade names Dow Corning 244®, 245®, 344® and 200® Fluids. Examples of silicone oils which can be used according to the invention are in particular those known under the INCI names dimethicone, methyl trimethicone, phenyl trimethicone, diphenylsiloxy phenyl trimethicone and caprylyl methicone.

Mention may in particular be made, among hydrocarbons, of linear or branched hydrocarbons comprising from 5 to 40 carbon atoms and preferably from 8 to 20 carbon atoms, such as pentane, hexane, heptane, decane, dodecane, tetradecane, tridecane and isoparaffins comprising from 8 to 20 carbon atoms, such as isododecane, isohexadecane, hydrogenated polyisobutene and hydrocarbons described in U.S. Pat. No. 3,439,088 and U.S. Pat. No. 3,818,105.

The hydrocarbons which are particularly preferred have the following physicochemical properties:
- a molecular weight of between approximately 70 and approximately 225 g/mol, preferably of between 160 and 190 g/mol,
- a boiling point of between approximately 30° C. and approximately 320° C., preferably of between approximately 60° C. and approximately 260° C., and
- a viscosity of approximately less than $10^{-5}$ m$^2$/s (10 centistokes) at 25° C.

For example, mention may be made of the hydrocarbons sold under the Isopars® brand by Exxon Mobil and the $C_{12}$ isoparaffins sold under the Permethyl® 99A brand by Permethyl Corporation.

Mention may in particular be made, as synthetic (poly) esters and (poly)ethers, of the (poly)esters of $C_5$-$C_{20}$ acids and $C_6$-$C_{20}$ alcohols which are advantageously branched, such as isononyl isononanoate or isostearyl neopentanoate, and also esters of hydroxy acids, such as diisostearyl malate, and polyesters of polyols.

Examples of vegetable oils comprise wheat germ, sunflower, grape seed, sesame, maize, apricot, castor, shea, avocado, olive, soybean, sweet almond, palm, rapeseed, cottonseed, hazelnut, macadamia, jojoba, alfalfa, poppy, pumpkinseed, cucumber, blackcurrant, evening primrose, millet, barley, quinoa, rye, safflower, candlenut, passionflower, musk rose or tea seed oil, and their mixtures.

As indicated above, the composition according to the invention can additionally include fatty-phase structuring agents, in particular at least one polar wax chosen from animal waxes, vegetable waxes, synthetic waxes including polar groups, such as esters, and silicone waxes including polar groups, such as ester groups. Mention may thus be made of carnauba wax, candelilla wax, beeswax (*cera alba*), Chinese insect (*Ericerus pela*) waxes, triesters of $C_8$-$C_{20}$ acids and of glycerol, such as glyceryl tribehenate, acetylated glycol stearate, sold in particular by Vevy under the trade name Cetacene®, and their mixtures. As a variant or in addition, the composition according to the invention can comprise nonpolar waxes, such as paraffin, polymethylene, polyethylene or polybutene waxes, microcrystalline waxes, ozokerite, silicone waxes and their mixtures. Other fatty-phase structuring agents are sucrose polyesters and olefinic copolymers.

Examples of lipophilic gelling agents are in particular modified clays, and also silicone polymers and more particularly organopolysiloxane elastomers. Mention may be made, among these, of noncyclic and at least partially crosslinked polymers resulting from the reaction of an organopolysiloxane carrying unsaturated groups, such as vinyl or allyl groups, situated at the end or in the middle of the chain, preferably on its silicon atom, with another reactive silicone compound, such as an organohydropolysiloxane. These polymers are usually available in the form of a gel in a volatile or nonvolatile silicone solvent or in a hydrocarbon solvent. Examples of such elastomers are sold in particular by Shin-Etsu under the trade names KSG-6®, KSG-16®, KSG-31®, KSG-32®, KSG-41®, KSG-42®, KSG-43® and KSG-44®, by Dow Corning under the trade names DC 9040®, DC 9041®, EL 8050 ID® and EL 8051 IN® and by Grant Inc. under the trade name Gransil®. These elastomers can be in the form of a powder or gel or predispersion in an appropriate solvent. Mention may also be made, as examples of elastomers in the form of powders, of those sold in particular by Dow Corning under the references EP 9215, EP 9261 Ti (coated with titanium dioxide), EP 9289 LL (coated with lauroyllysine), and EP 9293 AL (coated with aluminium).

Mention may be made, among hydrophilic gelling agents, of clays and AMPS (acrylamidomethylpropanesulphonic acid) copolymers.

The composition according to the invention can also include one or more pasty compounds, that is to say lipophilic fatty substances which, like waxes, are capable of undergoing a reversible liquid/solid change in state and have, in the solid state, an anisotropic crystalline arrangement but which differ from waxes in that they include, at a temperature of 23° C., a liquid fraction and a solid fraction.

It can additionally comprise at least one pressure sensitive adhesive (PSA). These are adhesives which, under pressure, spread out and completely wet the surface on which they are placed. A great many interactions then occur with the support, resulting in good adhesion. However, the interactions brought about are weak and can be overcome mechanically fairly easily. Such molecules are in particular obtained by condensation of a PDMS having an OH ending with an MQ silicate resin in a solvent, such as heptane. The Resin/PDMS ratio regulates the tack of the product. These products are sold, for example, by Dow Corning under the name PSA® and Bio PSA®. The preferred references are DC7-4505®, DC7-4405® and DC7-4411®, sold by Dow Corning.

The composition according to the invention can additionally comprise at least one film-forming polymer capable of contributing hold and/or transfer-free properties to the make-up conferred by the composition. The film-forming polymer can in particular be a cyclic silicone copolymer optionally modified by urethane or fluorine or acrylate, such as those sold by JEEN under the trade name Jeesilc® PS (including PS-VH, PS-VHLV, PS-CM, PS-CMLV and PS-DMLV), silicone (meth)acrylates, sold by Shin-Etsu under the trade names KP-545®, KP-561® and KP-562®, or the polymers sold by Dow Corning under the trade names DC FA 4002 ID® and DC FA 4001 CM®.

Other examples of film-forming polymers are silicone resins and in particular MQ resins, such as trimethylsiloxysilicates, and MT resins, such as silsesquioxane derivatives and in particular polymethylsilsesquioxanes, sold in particular by Shin-Etsu, and also polypropylsilsesquioxane, sold by Dow Corning under the trade name DC 670®, or phenylpropyl polysilsesquioxane, sold by Wacker under the trade name Belsil® SPR 45 VP. Another example is composed of the fluorosilicone polymers identified by the INCI name trifluoropropyldimethylsiloxy triethylsiloxysilicate, such as that sold by Momentive under the trade name XS66-B8226®. Other examples of film-forming polymers are poly(cyclic olefin)s, such as polycyclopentadiene, in particular sold by KOBO under the trade name Koboguard® 5400, or polydicyclopentadiene. Yet other examples of film-forming polymers are composed of copolymers of vinylpyrrolidone (VP) and of linear olefins, such as VP/hexadecene and VP/eicosene copolymers, including Antaron® V216 and Antaron® V220 from ISP, or also ethylene/vinyl acetate copolymers, such as AC® 400 from Baerlocher. Other film-forming polymers capable of being used in this invention are polyacrylates, such as poly(ethyl acrylate), sold in particular by Créations Couleurs under the trade name Creasil® 7 ID.

In the case where the composition is provided in the form of an emulsion, it is clearly understood that the composition according to the invention can also comprise one or more water-in-oil emulsifiers preferably chosen from nonionic surfactants, such as polyol polyesters, in particular polyethoxylated (30 EO) dipolyhydroxystearate, sold in particular under the trade name Arlacel® P135 by Uniqema, or polyglyceryl-4 diisostearate; polysiloxanes modified by polyethers, optionally carrying one or more alkyl groups, for example PEG-10 dimethicone, sold under the reference KF 6017® by Shin-Etsu, cetyl PEG/PPG-10/1 dimethicone or lauryl PEG-9 polydimethylsiloxyethyl dimethicone; and/or one or more oil-in-water emulsifiers chosen from nonionic surfactants, such as optionally polyethoxylated sorbitan esters, esters of fatty acids and of glycerol, esters of fatty acids and of sucrose, esters of fatty acids and of polyethylene glycol, polysiloxanes modified by polyether, such as PEG-11 methyl ether dimethicone, sold under the brand KF 6011® by Shin-Etsu, or PEG-12 dimethicone, sold by Dow Corning under the reference DC 5329®, silicone elastomers modified by polyether, ethers of fatty alcohols and of polyethylene glycol, alkylpolyglycosides and hydrogenated lecithin, and also their mixtures.

"Fillers" should be understood as meaning colourless or white, inorganic or synthetic and lamellar or nonlamellar particles intended to give body or stiffness to the composition and/or softness, mattness and uniformity immediately on application. Mention may in particular be made, as fillers, of talc, mica, silica, kaolin, Nylon® powders, such as Nylon-12 powders, for example sold under the brand Orgasol® by Arkema, polyethylene powders, polyurethane powders, polystyrene powders, polyester powders, composite powders, such as the powder formed of mica coated with aluminium hydroxide, sold under the brand Excel Mica JP2® by Miyoshi Kasei, optionally modified starch, silicone resin microbeads, such as, for example, those sold by Toshiba under the name Tospearl®, hydroxyapatite and silica microspheres, for example sold under the brand Silica Beads® by Maprecos, Spherica® by SACI-CFPA, Sunsil® by Warwick Adriss, Sunsphere® by IMCD or Creaspheres SIL ML9® by Cosmo Chem.

The colouring materials can be chosen from water-soluble or fat-soluble dyes, inorganic pigments, pearlescent agents, lakes and their mixtures. These colouring materials can optionally be treated at the surface with a hydrophobic agent, such as silanes, silicones, fatty acid soaps, $C_{9-15}$ fluoroalcohol phosphates, acrylate/dimethicone copolymers, mixed $C_9$-$C_{15}$ fluoroalcohol phosphate/silicone copolymers, lecithins or hydrogenated lecithin, carnauba wax, polyethylene, chitosan and optionally acylated amino acids, such as lauroyl lysine, disodium stearoyl glutamate and aluminium acyl glutamate.

"Pigments" should be understood as meaning white or coloured and inorganic or organic particles which are insoluble in the medium, which are intended to colour and/or opacify the composition and which have a conventional or nanometric size. Mention may be made, among inorganic pigments, of titanium, zirconium or cerium dioxides, and also zinc, iron or chromium oxides. The composition can comprise 3D Tech® composite pigments sold by Daito Kasei, which are PMMA hemispheres coated with inorganic or organic pigments. Use may be made, as "pearlescent agents or interference pigments", of iridescent particles which reflect light. Mention may be made, among the pearlescent agents which can be envisaged, of natural mother-of-pearl, mica covered with titanium dioxide, with iron oxide, with natural pigment or with bismuth oxychloride, and also coloured titanium oxide-coated mica. Use may also be made of pearlescent agents, the support of which is not natural mica but synthetic mica (synthetic fluorphlogopite) or glass (borosilicate).

The composition can also include "tightening agents", that is to say compounds capable of having a tightening effect, that is to say which can tauten the skin and, by this tightening effect, smooth the skin and reduce, indeed even bring about the disappearance, immediately, of wrinkles and fine lines. Mention may be made, as tightening agents, of polymers of natural origin, in particular vegetable origin, such as proteins and protein hydrolysates, and more particularly cereal, leguminous and oleaginous extracts, such as extracts of maize, rye, wheat, buckwheat, sesame, spelt, peas, broad beans, lentils, soybeans and lupin. Mention may also be made of synthetic polymers which are generally provided in the form of a latex or of a pseudolatex, such as the copolymer of PVP/dimethiconylacrylate and of hydrophilic polyurethane, for example sold under the brand Aquamere® S-2011 by Hydromer.

The composition according to the invention can additionally comprise at least one UV screening agent chosen from organic and inorganic screening agents and their mixtures. Mention may in particular be made, as organic screening agents, of dibenzoylmethane derivatives (including butyl methoxydibenzoylmethane), cinnamic acid derivatives (including ethylhexyl methoxycinnamate), salicylates, para-aminobenzoic acids, β,β-diphenylacrylates, benzophenones, benzylidenecamphor derivatives, phenylbenzimidazoles, triazines, phenylbenzotriazoles and anthranilic derivatives. Mention may in particular be made, as inorganic screening agents, of screening agents based on inorganic oxides in the form of pigments or nanopigments, which may or may not be coated and in particular based on titanium dioxide or zinc oxide.

Examples of adjuvants described above are mentioned in particular in the CTFA Dictionary (International Cosmetic Ingredient Dictionary and Handbook, published by The Cosmetic, Toiletry and Fragrance Association, 11$^{th}$ Edition, 2006).

The composition of the invention can be used as product for making up the skin. "Product for making up the skin" is understood to mean a cosmetic composition comprising, in a physiologically acceptable medium, at least one colouring material in an amount sufficient to colour the skin. Mention may in particular be made of a foundation, a complexion corrector, a concealer and a loose or compact powder, such as in particular a two-way cake.

The composition of the invention can also be used as product for caring for the skin. "Product for caring for the skin" is understood to mean a cosmetic composition which is devoid of colouring material and which provides the skin with at least one aesthetic advantage, generally by activating certain biological mechanisms. Mention may in particular be made of a moisturizing care product, an antiageing care product, in particular an antiwrinkle and/or firming product, a depigmenting product, a slimming product or a sun protection product.

Another subject-matter of the invention is thus the above-mentioned uses of the composition described above.

A further subject-matter of the invention is a cosmetic method for making up or caring for the skin, comprising the topical application to the latter, in particular to the face, neck, shoulders, hands and/or legs, of the composition described above.

The invention will now be illustrated by the following nonlimiting examples, which are given only for the purposes of illustration and do not have the aim of limiting the scope of the invention, which is defined by the appended claims.

EXAMPLES

Example 1

Preparation of PMMA-Based Compositions

A—Preparation of Foundations

A foundation according to the invention (Example 1) was prepared in the form of a water-in-silicone emulsion having the composition shown in Table 1 below, in which the proportions of the ingredients are expressed as percentages by weight.

Three Comparative Examples 1A, 1B and 1C of foundations were also prepared having the compositions shown in Table 1 below, in which the proportions of the ingredients are also expressed as percentages by weight.

TABLE 1

| | Foundations | | | |
|---|---|---|---|---|
| Chemical name or INCI NAME/ COMMERCIAL NAME | Comp. Example 1A (%) | Comp. Example 1B (%) | Comp. Example 1C (%) | Example 1 (%) |
| Pigments | 8 | 8 | 8 | 8 |
| Silicone oils | 25.5 | 25.5 | 25.5 | 25.5 |
| PEG-10 DIMETHICONE/ KF-6017 ® | 6.0 | 6.0 | 6.0 | 6.0 |
| HYDROGENATED POLYISOBUTENE & DISTEARDIMONIUM HECTORITE & PROPYLENE CARBONATE/ HECTONE DF ® | 2.0 | 2.0 | 2.0 | 2.0 |
| SPHERICAL PMMA/ COVABEAD ® | 5.0 | — | — | — |
| Hemispherical PMMA (a) | — | 5.0 | — | 2.5 |
| Coated hemispherical PMMA (b) | — | — | 5.0 | 2.5 |

TABLE 1-continued

Foundations

| Chemical name or INCI NAME/ COMMERCIAL NAME | Comp. Example 1A (%) | Comp. Example 1B (%) | Comp. Example 1C (%) | Example 1 (%) |
|---|---|---|---|---|
| Preservatives | 3.00 | 3.0 | 3.0 | 3.0 |
| 1,3-BUTYLENE GLYCOL | 5.0 | 5.0 | 5.0 | 5.0 |
| WATER | 45.0 | 45.0 | 45.0 | 45.0 |
| SODIUM CHLORIDE | 0.5 | 0.5 | 0.5 | 0.5 |
| Total | 100.0 | 100.0 | 100.0 | 100.0 |

B—Preparation of an Anhydrous Gel

An anhydrous gel (Example 2) according to the invention was prepared having the composition (as percentages by weight) shown in Table 2 below.

TABLE 2

Anhydrous gel

| Chemical name or INCI NAME | % |
|---|---|
| DIMETHICONE/VINYL DIMETHICONE CROSSPOLYMER & ISOCETETH-10 | 14.15 |
| SYNTHETIC WAX | 10.15 |
| NEOPENTYL GLYCOL DIOCTANOATE | 16.85 |
| Coated hemispherical PMMA (b) | 1.25 |
| Hemispherical PMMA (a) | 1.25 |
| ISODECYL NEOPENTANOATE & DIMETHICONE/BIS-ISOBUTYL PPG-20 CROSSPOLYMER | 56.35 |

C—Preparation of Anhydrous Foundations

An anhydrous foundation (Example 3) according to the invention, including hemispherical particles (a) and (b), was prepared, and also a foundation including PMMA spheres (Comparative Example 3), each having the composition (as percentages by weight) shown in Table 3 below.

To do this, all the ingredients were weighed out and were then heated at 85-90° C. until the waxes had melted. The mixture was subsequently passed 3 times through a roll mill and was then reheated to 85° C. before being cast in dishes.

TABLE 3

Anhydrous foundations

| Chemical name or INCI NAME | Example 3 % | Comp. Example 3 % |
|---|---|---|
| Oils | 50.7 | 50.7 |
| Polar waxes | 5.1 | 5.1 |
| Nonpolar wax | 5.0 | 5.0 |
| Preservatives | 1.0 | 1.0 |
| Antioxidants | 0.2 | 0.2 |
| TALC | 10.0 | 10.0 |
| POLYMETHYL METHACRYLATE | 0 | 10 |
| Hemispherical PMMA (a) | 5 | 0 |
| Coated hemispherical PMMA (b) | 5 | 0 |
| ALUMINIUM STARCH OCTENYLSUCCINATE | 10.0 | 10.0 |
| Pigments | 8.0 | 8.0 |

D—Preparation of a Moisturizing Product

A moisturizing care product (Example 4) according to the invention, in the form of an O/E emulsion, including hemispherical particles (a) and (b), was prepared. It had the composition (as percentages by weight) shown in Table 4 below.

TABLE 4

Moisturizing product

| Chemical name or INCI NAME | Example 4 (%) |
|---|---|
| WATER | q.s. for 100% |
| TETRASODIUM EDTA | 0.05 |
| Humectants | 13.00 |
| Preservatives | 0.60 |
| Hydrophilic gelling agent | 1.20 |
| ISOHEXADECANE | 5.00 |
| PPG-2 MYRISTYL ETHER PROPIONATE | 5.00 |
| Tightening agent | 2.00 |
| ALCOHOL | 5.00 |
| pH adjuster | q.s. |
| Hemispherical PMMA (a) | 3.50 |
| Coated hemispherical PMMA (b) | 3.50 |

E—Preparation of a W/Si Foundation

A foundation according to the invention (Example 5), in the form of W/Si emulsion, including hemispherical particles (a) and (b), was prepared. It had the composition (as percentages by weight) shown in Table 5 below.

TABLE 5

Foundation

| Chemical name or INCI NAME | % |
|---|---|
| Coated pigments | 11.0 |
| Silicone oils | 19.5 |
| W/Si emulsifier | 6 |
| UV screening agents | 10.5 |
| Lipophilic gelling agents | 2 |
| Humectants | 6.7 |
| Preservatives | q.s. |
| WATER | q.s. for 100 |
| SODIUM CHLORIDE | 0.5 |
| Coated hemispherical PMMA (b) | 3 |
| Hemispherical PMMA (a) | 3 |
| Pearlescent agents | 3 |
| Pressure-sensitive adhesive | 2 |

Example 2

Sensory Analysis

The compositions of Example 1 according to the invention and of Comparative Examples 1A, 1B and 1C were evaluated in sensory analysis by a trained panel.

The test protocol used was as follows.

Between 16 and 18 judges tested the formulations under specific conditions of luminosity (daylight combined with a halogen light). They evaluated the following descriptors, the possible values of which are shown between brackets.

Luminosity: Presence of areas which reflect light (Not luminous, Very luminous).

Homogeneity of the complexion: Uniformity in the complexion over the entire face (Not uniform to Very uniform)

Size of the pores (Small to Big)

Olive, beige, red.

The evaluations were carried out on half a face. For each sample, the procedure was as follows: 0.15 ml of product was applied to half the face, including the edge of the neck. The product was then allowed to dry for 5 minutes.

The effectiveness of the products with regard to the radiance of the complexion was subsequently evaluated according to the CLCT™ method developed by SpinControl. The method is published in the document entitled "Visual Evaluation in vivo of Complexion Radiance Using the CLBT Sensory Method", C. Musnier et al., *Skin Research and Tech.*, Vol. 10, pp. 50-56 (2004).

According to this method, an increase in the radiance is reflected by (with comparison to naked skin):
- a limited decrease (if foundation) or even an increase (if skin care product) in the red;
- a reduction in the olive down to an optimum of 0;
- a lack of increase in the beige (if foundation);
- an increase in the luminosity up to an optimum of 10;
- an increase in the homogeneity up to an optimum of 10;
- a reduction in the size of the pores down to an optimum of 0.

The results obtained are combined in Table 6 below. The figures shown correspond to the difference in the values of the descriptors evaluated before and after application of the composition to the skin.

TABLE 6

| | | Sensory analysis | | | | |
|---|---|---|---|---|---|---|
| Composition | Luminosity | Homogeneity | Size of the pores | Red | Olive | Beige |
| Comp. Example 1A | — | +1.0 | −0.3 | −0.9 | +0.4 | +0.6 |
| Comp. Example 1B | — | +1.2 | — | −1.2 | — | +0.9 |
| Comp. Example 1C | — | +1.1 | −0.5 | −1.4 | +0.3 | +0.8 |
| Example 1 | +0.3 | +1.1 | −0.3 | −1.1 | — | — |

The results obtained indicate that the composition of Example 1, which comprises the combination of the 2 hemispherical powders (a) and (b), makes it possible to correct failings which are not corrected by each of the compositions of Comparative Examples 1A, 1B and 1C. Specifically, the results obtained correspond to an improvement in the radiance for 5 descriptors out of 6.

Thus, Example 1 of the invention is the only composition among those evaluated which, when it is applied to the skin, is evaluated as:
- luminous (+0.3);
- improving the soft focus effect (the size of the pores is reduced by −0.3);
- improving the homogeneity of the skin (+1.1);
- not reducing the beige;
- not increasing the olive.

Comparative Example 1A is less effective with regard to the radiance as luminosity is not increased and the olive is increased.

Comparative Example 1B is less effective with regard to the radiance as the luminosity is not increased and the size of the pores is not reduced.

Comparative Example 1C is less effective with regard to the radiance as the luminosity is not increased and the olive is increased.

The results presented in Table 6 thus clearly show that, by virtue of the combination of (a) uncoated hemispherical PMMA particles and (b) hemispherical PMMA particles coated with titanium dioxide, the composition of Example 1 of the invention contributes significantly more radiance to the skin.

Moreover, a sensory analysis was performed by a trained panel on the compositions of Example 3 and comparative Example 3, which showed that Example 3 provided for better skin glow and smoothness.

The invention claimed is:

1. A cosmetic composition, comprising a combination of:
(a) uncoated hemispherical polymethylmethacrylate particles; and
(b) hemispherical polymethylmethacrylate particles coated with titanium dioxide,
   wherein the particles of (a) and of (b) are combined in a ratio by weight of (a) to (b) of between 20/80 and 80/20.

2. The cosmetic composition according to claim 1, wherein the titanium dioxide has a primary particle size of between 1 nm and 100 nm.

3. The cosmetic composition according to claim 1, wherein the titanium dioxide is treated with at least one compound selected from the group consisting of silicone derivatives, triethoxycaprylylsilane, titanates, esters, fluorinated compounds, and mixtures thereof.

4. The cosmetic composition according to claim 1, wherein the titanium dioxide is treated with triethoxycaprylylsilane.

5. The cosmetic composition according to claim 1, wherein the titanium dioxide coating of the polymethylmethacrylate represents from 10 to 40% by weight with respect to the total weight of the polymethylmethacrylate/titanium dioxide composite.

6. The cosmetic composition according to claim 1, wherein the combination of the substantially hemispherical particles (a) and (b) represents from 1 to 60% by weight with respect to the total weight of the composition.

7. A method of making up the skin, comprising applying to the skin the composition according to claim 1 as foundation, complexion corrector, concealer or loose or compact powder.

8. A method of caring for the skin, comprising applying to the skin an effective amount of the composition according to claim 1 as a moisturizing care product, antiageing care product, antiwrinkle product, firming product, depigmenting product, slimming product or sun protection product.

9. A cosmetic method for making up or caring for the skin, comprising topical application to the skin of the composition according to claim 1.

10. The cosmetic composition according to claim 2, wherein the titanium dioxide is treated with at least one compound selected from the group consisting of silicone derivatives, triethoxycaprylylsilane, titanates, esters, fluorinated compounds, and mixtures thereof.

11. The cosmetic composition according to claim 2, wherein the titanium dioxide is treated with triethoxycaprylylsilane.

12. The cosmetic composition according to claim 3, wherein the titanium dioxide is treated with triethoxycaprylylsilane.

13. The cosmetic composition according to claim 2, wherein the titanium dioxide coating of the polymethylmethacrylate represents from 10 to 40% by weight with respect to the total weight of the polymethylmethacrylate/titanium dioxide composite.

14. The cosmetic composition according to claim 3, wherein the titanium dioxide coating of the polymethylmethacrylate represents from 10 to 40% by weight with respect to the total weight of the polymethylmethacrylate/titanium dioxide composite.

15. The cosmetic composition according to claim 4, wherein the titanium dioxide coating of the polymethylmethacrylate represents from 10 to 40% by weight with respect to the total weight of the polymethylmethacrylate/titanium dioxide composite.

* * * * *